(12) United States Patent
Martin

(10) Patent No.: US 8,083,742 B2
(45) Date of Patent: Dec. 27, 2011

(54) INTRAMEDULLARY NAIL

(75) Inventor: Daniel L Martin, Palo Alto, CA (US)

(73) Assignee: Synthes USA, LLC, West Chester, PA (US)

( * ) Notice: Subject to any disclaimer, the term of this patent is extended or adjusted under 35 U.S.C. 154(b) by 943 days.

(21) Appl. No.: 10/529,139

(22) PCT Filed: Sep. 27, 2002

(86) PCT No.: PCT/CH02/00538
§ 371 (c)(1),
(2), (4) Date: May 4, 2006

(87) PCT Pub. No.: WO2004/028383
PCT Pub. Date: Apr. 8, 2004

(65) Prior Publication Data
US 2006/0235394 A1    Oct. 19, 2006

(51) Int. Cl.
*A61B 17/58*    (2006.01)
*A61F 2/30*    (2006.01)
(52) U.S. Cl. .......................................................... 606/64
(58) Field of Classification Search ................ 606/62–64
See application file for complete search history.

(56) References Cited

U.S. PATENT DOCUMENTS

| | | | | |
|---|---|---|---|---|
| 2,675,801 A | * | 4/1954 | Bambara et al. ................ | 606/62 |
| 2,821,979 A | * | 2/1958 | Cameron ........................ | 606/64 |
| 3,670,724 A | * | 6/1972 | Bosacco ......................... | 606/64 |
| 4,475,545 A | * | 10/1984 | Ender ............................. | 606/64 |
| 4,622,959 A | * | 11/1986 | Marcus ........................... | 606/64 |
| 4,653,487 A | * | 3/1987 | Maale ............................. | 606/62 |
| 5,041,115 A | * | 8/1991 | Frigg et al. ..................... | 606/62 |

(Continued)

FOREIGN PATENT DOCUMENTS

DE    20002988    5/2000

OTHER PUBLICATIONS

Kaoru Endo, Kozo Nakamura, Hiroto Maeda and Takashi Matsushita "Interlocking Intramedullary Nail Method for the Treatment of Femoral and Tibial Fractures in Cats and Small Dogs". J. Vet. Med. Sci.. vol. 60: 119-122. (1998).*

*Primary Examiner* — Anu Ramana
(74) *Attorney, Agent, or Firm* — Fay Kaplun & Marcin, LLP

(57) ABSTRACT

The intramedullary nail has a longitudinal axis (5), a near end (1) with means (8) for coupling to an insertion device and a far end (2) with a tip (7) for insertion into the intramedullary canal of a long bone. The far end (2) is provided with at least two traversing through holes (3) with axes (6), all of said through holes (3) being grouped in said far end (2) within a distance x measured from said tip (7) to the axis (6) of the most distant hole (3). The nail is provided with at least a third through hole (3) with axis (6) in said far end (2) which contains the first and second holes (3) and the projection of the hole axis (6) of said through holes (3) in a plane orthogonal to said longitudinal axis (5) is such that at least two of said projected hole axis (6) are at an angle α greater than zero and less than 90° with respect to each other.

27 Claims, 2 Drawing Sheets

U.S. PATENT DOCUMENTS

| | | | |
|---|---|---|---|
| 5,102,413 A * | 4/1992 | Poddar | 606/62 |
| 5,248,313 A * | 9/1993 | Greene et al. | 606/62 |
| 5,458,654 A * | 10/1995 | Tepic | 606/62 |
| 5,472,444 A | 12/1995 | Huebner et al. | |
| 5,766,174 A * | 6/1998 | Perry | 606/62 |
| 6,010,506 A | 1/2000 | Gosney et al. | |
| 6,120,504 A | 9/2000 | Brumback et al. | |
| 6,197,065 B1 * | 3/2001 | Martin et al. | 623/23.17 |
| 6,210,414 B1 | 4/2001 | Lin | |
| 6,221,074 B1 * | 4/2001 | Cole et al. | 606/62 |
| 6,270,499 B1 | 8/2001 | Leu et al. | |
| 6,296,645 B1 * | 10/2001 | Hover et al. | 606/62 |
| 6,547,791 B1 | 4/2003 | Buhren et al. | |
| 6,551,321 B1 * | 4/2003 | Burkinshaw et al. | 606/62 |
| 6,702,816 B2 | 3/2004 | Buhler | |
| 6,808,527 B2 * | 10/2004 | Lower et al. | 606/62 |
| 2002/0103488 A1 * | 8/2002 | Lower et al. | 606/62 |
| 2002/0151898 A1 | 10/2002 | Sohngen et al. | |
| 2002/0183750 A1 * | 12/2002 | Buhler | 606/62 |
| 2003/0069581 A1 | 4/2003 | Stinson et al. | |
| 2003/0195515 A1 * | 10/2003 | Sohngen | 606/62 |
| 2006/0111716 A1 * | 5/2006 | Schlienger et al. | 606/64 |
| 2007/0016203 A1 * | 1/2007 | Schlienger et al. | 606/64 |

\* cited by examiner

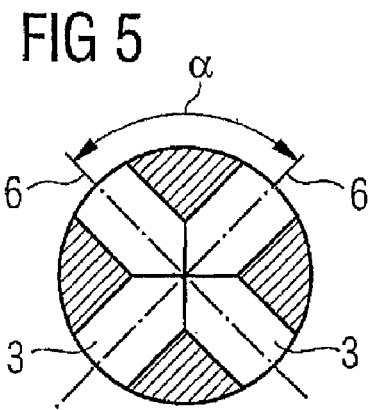
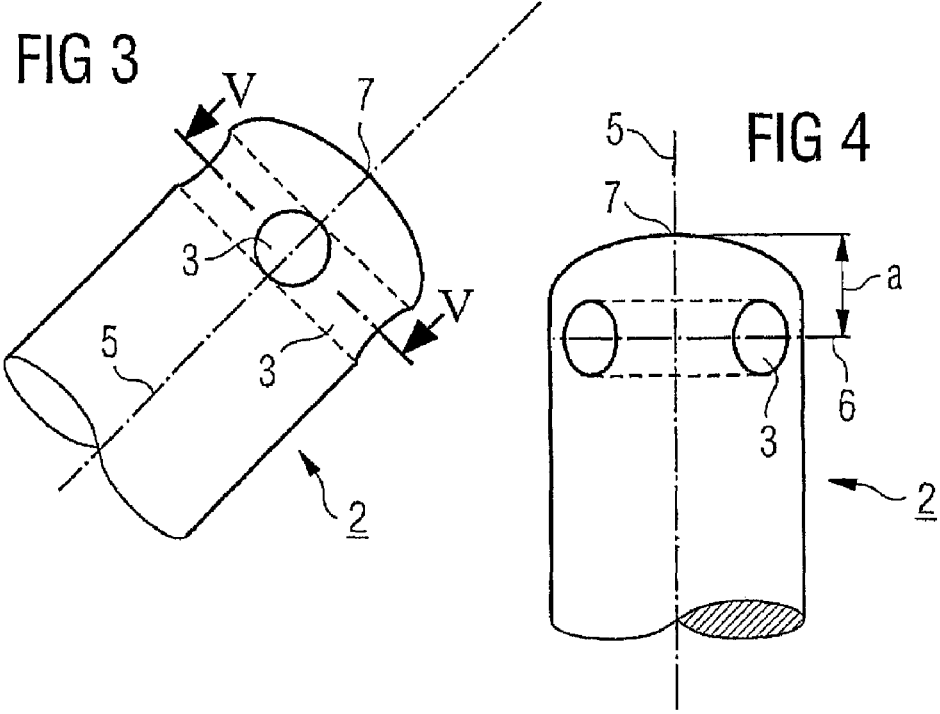
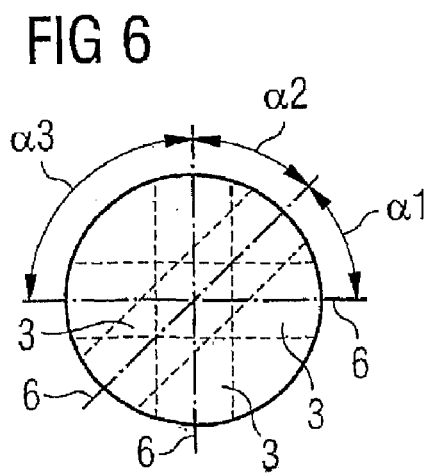

INTRAMEDULLARY NAIL

FIELD OF THE INVENTION

This invention concerns an intramedullary nail and, more particularly, an intramedullary nail having a plurality of transverse holes extending through a distal end of the nail.

BACKGROUND OF THE INVENTION

Such a nail is known from German patent publication DE-C-3 244 243 to ENDER, which discloses a rigid intramedullary nail having two through holes at the distal end of the nail and whose direction is not parallel and not orthogonal and which is further defined in the specification to be at an acute angle, e.g., of 10° or 60°.

A further nail is known from U.S. Pat. No. 5,041,115 to FRIGG et al., which discloses an intramedullary nail having three through holes at the distal end of the nail which are disposed at 90° to each other.

A disadvantage of the known nails is the fact that the distal holes are unnecessarily far from the distal nail tip which produces a nail-weakening effect, and prevents engagement in very short distal fragments.

A further disadvantage of the known nails having parallel holes spaced closely to one another (i.e., known nail hole spacings equal to 3.5(d)) is the fact that holes in the bone surface are too close to one another.

Still a further disadvantage is that widely spaced parallel or orthogonal holes offer the surgeon limited options in the choice of the position of the screws, such as might be necessary to avoid neurovascular structures.

A further disadvantage of these known nails is the fact that there is an unnecessary loose fit to the hole in the nail by the screws which traverse the nail. This allows a toggling of the traversing screw in the hole, in turn allowing an increased torsional twisting and other motion at the fracture site.

The invention as claimed aims at solving the above described problems/disadvantages and also aims to facilitate secure attachment in short fragments at the distal end of the intramedullary nail.

SUMMARY OF THE INVENTION

The present invention provides an intramedullary nail comprising a nail body having a longitudinal axis, a proximal end configured and dimensioned for coupling to an insertion device, and a distal end having a tip configured and dimensioned for insertion into the intramedullary canal of a long bone. At least three transverse holes extend through the distal end of the nail body, with each transverse hole defining a hole axis, and all three transverse holes grouped at the distal end within a distance x measured from the tip of the nail body to the axis of the transverse hole furthest from the tip. A projection of the three hole axes of the at least three transverse holes in a plane orthogonal to the longitudinal axis is such that at least two of the projected hole axes are at an angle $\alpha$ with respect to one another, where $0 < \alpha < 90°$, and where the distance $x \leq 25d$, where d is either the diameter of the largest of the at least three transverse holes or d is the mean diameter of the at least three holes.

Surprisingly, mechanical and clinical studies undertaken by the inventor, have revealed that of two different intramedullary nails having the same number of traversing holes clustered near the distal tip of the nail, the one with holes clustering closer to the tip of the nail is less likely to face failure through a screw hole than the intramedullary nail with greater hole spacing. Furthermore unused holes between the nail tip and x-position do not weaken the nail more than does the x-position hole. This is true for the same diameter.

The x-position hole is the hole in the far half of the intramedullary nail which is farthest from the tip of the nail.

The multiple hole/close spacing intramedullary nail according to the invention can be used for all known applications, i.e., proximal fracture, extreme distal fracture, ankle fusion and correction of deformity and therefore replaces all known nails with one single type, making storage much simpler and less costly. It maximizes the number of screws which can be placed near the tip of the nail, increasing the surface contact area between the hardware and the bone.

The invention offers the following advantages:

1) it prevents adjacent screws from having their bone cortex holes too close to one another—thereby reducing crack propagation between these bone cortex holes;

2) it gives the surgeon different anatomical position options for placement of screws to provide more secure bony fixation or to allow avoidance of neurovascular structures; and 3) it controls angular motion of the fragment with respect to the intramedullary nail by way of a greater possible number of screws, screws in multiple directions, and closer fit of the screws in the holes.

In a preferred embodiment of the intramedullary nail, the distance x measured from the tip of the nail to the axis of the hole most distant from the tip is equal or smaller than 25d, preferably equal or smaller than 7d, d being the diameter of the holes.

In a preferred embodiment of the invention the projected hole axes of at least two of said through holes are at an angle $\alpha$ of approx. 30°, 36°, 45° or 60° or multiples thereof.

Preferably a number of $n \geq 4$ holes are grouped in the far end of the nail within a distance x which is smaller than $2(n)(d)$, d being the diameter of the holes. More preferably the value for x is smaller than $1.5(n)(d)$. In another embodiment, the value for x may be smaller than $1.8(n)(d)$. In yet another embodiment, the value for x may be smaller than $1.4(n)(d)$.

In a preferred embodiment the value of n for the number of holes is 5 or 6.

At least two through holes may be located in such a way that the geometric hollow cylinders, as defined by these holes, intersect with one another, preferably with intersecting axes of these cylinders. The two intersecting through holes may be located at the same distance d from said tip of the nail and preferably are spaced 88°-92° apart. In the above specified formulae for the distance x the two holes which intersect, only one should be included in the number n of holes.

In order to facilitate a more secure fixation with the interlocking screw having an outer thread at least one of the through holes may be provided with a matching internal thread. This facilitates more secure fixation with the interlocking screw having a matching outer thread.

Furthermore a portion of one or more screw holes may be substantially conical in geometry.

The intramedullary nail has preferably a solid cross-section, but may have alternatively a tubular cross-section.

Preferably all holes are located in planes orthogonal to the longitudinal axis of the nail.

The distance (a) between the tip of the nail and that through hole which nearest to the tip (7) may be (a)$\leq$5 d, and preferably (a)$\leq$1.5 d, whereby d is the diameter of the through hole.

In a preferred embodiment a plurality of n through holes are provided in the nail whose centres are located at a distance x from said tip which is comprised in the range of $$1.05(n)(d) \leq x \leq 3.00(n)(d)$$

In a further preferred embodiment a plurality of n through holes are provided in the nail whose centres are located at a distance x from the tip which is smaller than $4d+(n-1)(2.2\ d)$.

Preferably the distance "b" between the axes of two adjacent through holes is $b \leq 1.5\ d$.

The intramedullary nail according to the invention may comprise an interlocking screw which has a diameter equal or larger than 0.9 times the hole diameter into which it is inserted; preferably the diameter is equal or larger than 0.94, most preferably 0.96 times the hole diameter into which it is inserted.

BRIEF DESCRIPTION OF THE DRAWINGS

In the drawings:

FIG. 3 is an enlarged detailed view of the far end of intramedullary nail showing the core where holes intersect;

FIG. 4 is the same view of FIG. 3 rotated by 90°;

FIG. 5 is section along the line V-V of FIG. 3; and

FIG. 6 is a representation of a plane orthogonal to the longitudinal axis of the nail with projections of the axes of the through holes showing the various angles at which the through holes traverse the nail.

DETAILED DESCRIPTION OF THE PREFERRED EMBODIMENTS

Figure 1:
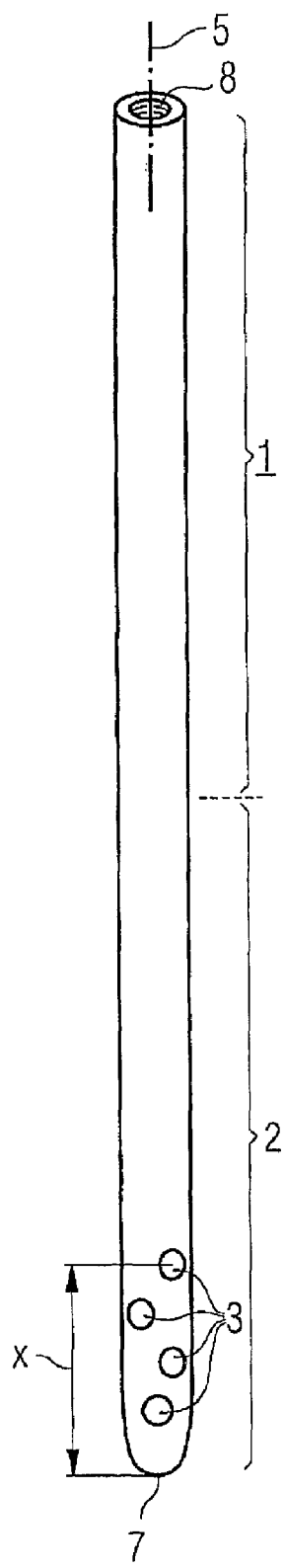
FIG. 1 is a side view of the intramedullary nail according to the invention.

FIG. 1 shows an intramedullary nail with a solid cross-section having a longitudinal axis 5. The longitudinal axis 5 may be curved along a portion of the nail if the nail itself is curved in that portion. The intramedullary nail further comprises a near end 1 with means 8 consisting of an internally threaded bore for coupling to an insertion device and a far end 2 with a tip 7 for insertion into the intramedullary canal of a long bone. The far end 2 is provided with four traversing through holes 3 with axes 6, all of said through holes 3 being grouped in said far end 2 within a distance measured from said tip 7 to the axis 6 of the most distant hole 3 (as indicated by the arrow in FIG. 1).

Figure 2:
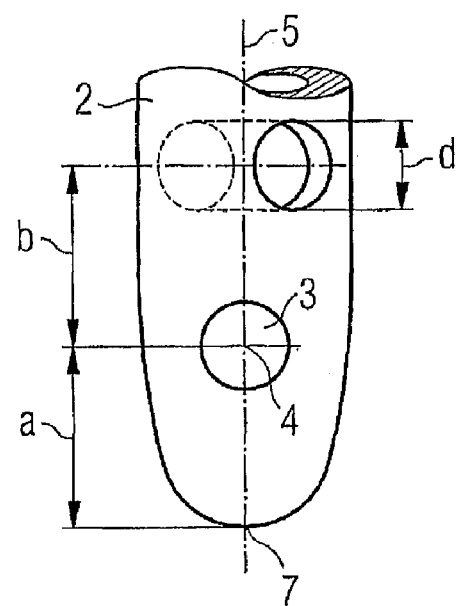
FIG. 2 is an enlarged detailed view of the far end of intramedullary nail of FIG. 1.

The projection of the hole axis 6 of said through holes 3 in a plane orthogonal to said longitudinal axis 5 (or if the hole axis 6—as shown in the figures—is lying already in an orthogonal plane, the hole axis itself) is such that at least two of said (projected) hole axes 6 are at an angle α greater than zero and less than 90° with respect to each other. In FIG. 2 the angle α is approximately 60°. In a first preferred embodiment, the angle α is $58° \leq \alpha \leq 62°$. In a second preferred embodiment, the angle α is $59° \leq \alpha \leq 61°$. In a third preferred embodiment, the angle α is $43° \leq \alpha \leq 47°$. In a fourth preferred embodiment, the angle α is $44° \leq \alpha \leq 46°$. In a fifth preferred embodiment, the angle α is $35° \leq \alpha \leq 37°$. In a sixth preferred embodiment, the angle α is $35.5° \leq \alpha \leq 36.5°$. In a seventh preferred embodiment, the angle α is $29° \leq \alpha \leq 31°$. In an eighth preferred embodiment, the angle α is $29.5° \leq \alpha \leq 30.5°$.

In the nail according to FIGS. 1 and 2, a number n of four holes 3 is grouped in said far end 2 within a distance x which is smaller than the product of $2(n)(d)$, d being the diameter of said holes 3.

In FIGS. 3 to 5 an embodiment is shown in which two of said through holes 3 are located in such a way that the geometric hollow cylinders, as defined by said holes 3, intersect with one another. In particular the two intersecting through holes 3 have intersecting axes 6 and are located at the same distance "a" from the tip 7. The two holes 3 are located in an orthogonal plane to said longitudinal axis 5 and are spaced at an angle α 90° apart.

FIG. 6 shows a representation of a plane orthogonal to the longitudinal axis 5 of the nail 1 with projections of the axis 6 of the through holes 3 showing the various angles $\alpha_1$, $\alpha_2$, and $\alpha_3$ in orthogonal projection at which the through holes 3 traverse the nail 1. The angles $\alpha_1$, $\alpha_2$, and $\alpha_3$ may be in the range of 30° to 60° according to the anatomy requirements.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

The invention claimed is:

1. An intramedullary nail comprising:
    a nail body having a longitudinal axis, a proximal end configured and dimensioned for coupling to an insertion device, and a distal end having a tip configured and dimensioned for insertion into the intramedullary canal of a long bone,
    at least three transverse holes extending through the distal end of the nail body, each transverse hole defining a hole axis, and all three transverse holes grouped at the distal end within a distance x measured from the tip of the nail body to the axis of the transverse hole furthest from the tip,
    wherein a projection of the three hole axes of the at least three transverse holes in a plane orthogonal to the longitudinal axis is such that at least two of the projected hole axes are at an angle α with respect to one another, where 0<α<90°, and where the distance x≦25d, where d is either the diameter of the largest of the at least three transverse holes or d is the mean diameter of the at least three holes.

2. The nail of claim 1, where the distance x≦7d.

3. The nail of claim 1, wherein at least two of the projected hole axes are at an angle α of $58° \leq \alpha \leq 62°$.

4. The nail of claim 1, wherein at least two of the projected hole axes are at an angle α of $59° \leq \alpha \leq 61°$.

5. The nail of claim 1, wherein at least two of the projected hole axes are at an angle α of $43° \leq \alpha \leq 47°$.

6. The nail of claim 1, wherein at least two of the projected hole axes are at an angle α of $44° \leq \alpha \leq 46°$.

7. The nail of claim 1, wherein at least two of the projected hole axes are at an angle α of $35° \leq \alpha \leq 37°$.

8. The nail of claim 1, wherein at least two of the projected hole axes are at an angle α of $35.5° \leq \alpha \leq 36.5°$.

9. The nail of claim 1, wherein at least two of the projected hole axes are at an angle α of $29° \leq \alpha \leq 31°$.

10. The nail of claim 1, wherein at least two of the projected hole axes are at an angle α of $29.5° \leq \alpha \leq 30.5°$.

11. The nail of claim 1, further comprising at least a fourth hole grouped at the distal end of the nail body within the distance x measured from the tip of the nail body to the axis of the transverse hole furthest from the tip.

12. An intramedullary nail comprising:
    a nail body having a longitudinal axis, a proximal end configured and dimensioned for coupling to an insertion device, and a distal end having a tip configured and dimensioned for insertion into the intramedullary canal of a long bone, at least three transverse holes extending through the distal end of the nail body, each transverse hole defining a hole axis, and all three transverse holes grouped at the distal end within a distance x measured from the tip of the nail body to the axis of the transverse hole furthest from the tip, wherein a projection of the three hole axes of the at least three transverse holes in a plane orthogonal to the longitudinal axis is such that at least two of the projected hole axes are at an angle $\alpha$ with respect to one another, where $0<\alpha<90°$, and where the distance $x<2(n)(d)$, where n is the number of transverse holes grouped within the distance x from the tip of the nail body and d is either the diameter of the largest of the at least three transverse holes or d is the mean diameter of the at least three holes.

13. The intramedullary nail of claim 12, wherein the distance $x<1.8(n)(d)$.

14. The intramedullary nail of claim 12, wherein the distance $x<1.5(n)(d)$.

15. The intramedullary nail of claim 12, wherein the distance $x<1.4(n)(d)$.

16. The intramedullary nail of claim 12, wherein the distal end of the nail includes at least five transverse holes grouped within the distance x, such that n=5.

17. The intramedullary nail of claim 12, wherein at least two of the transverse holes at least partially intersect one another.

18. The intramedullary nail of claim 17, wherein the at least two intersecting transverse holes are spaced at an angle $\alpha$ of 88°-92° with respect to one another.

19. The intramedullary nail of claim 12, wherein at least one of the transverse holes includes an internal thread.

20. The intramedullary nail of claim 12, wherein at least one of the transverse holes includes at least a portion with a conical shape.

21. The intramedullary nail of claim 12, wherein the nail body has a tubular cross-section.

22. The intramedullary nail of claim 12, wherein the axes of all transverse holes are located in planes orthogonal to the longitudinal axis of the nail body.

23. An intramedullary nail comprising:
a nail body having a longitudinal axis, a proximal end configured and dimensioned for coupling to an insertion device, and a distal end having a tip configured and dimensioned for insertion into the intramedullary canal of a long bone, at least three transverse holes extending through the distal end of the nail body, each transverse hole defining a hole axis, and all three transverse holes grouped at the distal end within a distance x measured from the tip of the nail body to the axis of the transverse hole furthest from the tip, wherein a projection of the three hole axes of the at least three transverse holes in a plane orthogonal to the longitudinal axis is such that at least two of the projected hole axes are at an angle $\alpha$ with respect to one another, where $0<\alpha<90°$, and where a distance a between the tip and the transverse hole closest to the tip is $a \leq 5d$ where d is the diameter of the transverse hole closest to the tip.

24. The intramedullary nail of claim 23, wherein the distance $a \leq 1.5d$.

25. The intramedullary nail of claim 23, wherein a plurality of n transverse holes are located in the nail body, and a center of each hole is located at a distance x from the tip of the nail body, where $1.05(n)(d) \leq x \leq 3.0(n)(d)$.

26. The intramedullary nail of claim 25, where $x<(4(d)+(n-1)(2.2d))$.

27. The intramedullary nail of claim 23, wherein a distance b between the axes of two adjacent transverse holes is $b \leq 1.5d$.

* * * * *